(12) United States Patent
Obradovic et al.

(10) Patent No.: US 11,485,691 B1
(45) Date of Patent: Nov. 1, 2022

(54) NON-CATALYTIC OXIDATIVE COUPLING OF METHANE

(71) Applicant: TOTALENERGIES ONETECH, Courbevoie (FR)

(72) Inventors: Ana Obradovic, Senefe (BE); Walter Vermeiren, Senefe (BE); Christophe Thille, Senefe (BE); Jean-Pierre Dath, Senefe (BE)

(73) Assignee: TOTALENERGIES ONETECH, Courbevoie (FR)

( * ) Notice: Subject to any disclaimer, the term of this patent is extended or adjusted under 35 U.S.C. 154(b) by 0 days.

(21) Appl. No.: 17/732,450

(22) Filed: Apr. 28, 2022

(30) Foreign Application Priority Data

Apr. 29, 2021 (EP) .................................... 21171121

(51) Int. Cl.
*C07C 2/82* (2006.01)
*B01J 12/00* (2006.01)

(52) U.S. Cl.
CPC ................ *C07C 2/82* (2013.01); *B01J 12/00* (2013.01)

(58) Field of Classification Search
None
See application file for complete search history.

(56) References Cited

U.S. PATENT DOCUMENTS

| | | | | |
|---|---|---|---|---|
| 4,950,827 A * | 8/1990 | Erekson | ..................... | C07C 2/84 585/921 |
| 5,214,226 A * | 5/1993 | Bauer | ....................... | C07C 2/82 585/700 |
| 5,935,533 A * | 8/1999 | Kleefisch | ............. | B01D 71/024 422/239 |
| 5,980,840 A * | 11/1999 | Kleefisch | ................ | C01B 3/382 422/204 |
| 10,941,088 B1* | 3/2021 | Sarsani | .................... | B01J 19/24 |
| 11,040,928 B1* | 6/2021 | Weissman | ............. | B01J 8/0257 |
| 2005/0124841 A1 | 6/2005 | Rapier et al. | | |
| 2009/0270640 A1* | 10/2009 | Maurer | ................ | C07D 301/10 549/523 |

(Continued)

FOREIGN PATENT DOCUMENTS

| EP | 0302665 A1 | 2/1989 |
|---|---|---|
| WO | 2018144370 A1 | 8/2018 |
| WO | 2018146591 A1 | 8/2018 |

OTHER PUBLICATIONS

Extended European Search report issued in Application No. 21171121.3 dated Oct. 20, 2021, 5 pages.

*Primary Examiner* — Ali Z Fadhel
(74) *Attorney, Agent, or Firm* — Ewing & Jones, PLLC

(57) ABSTRACT

The disclosure provides for a process for a non-catalytic oxidative coupling of methane reaction remarkable in that the process comprises a step of providing a counter-current shell-tube reactor comprising at least two tubes defining a tubular part and a shell part surrounding the tubular part and at least one inlet to feed a gaseous feed stream and at least one outlet to discharge a product stream; a step of providing a gaseous feed stream comprising a gas mixture of methane and oxygen in a defined molar ratio and preheated to a defined operating inlet temperature; a step of feeding the gaseous feed stream at least in the tubular part of the counter-current shell-tube reactor and a step of recovering a product stream.

15 Claims, 3 Drawing Sheets

(56) References Cited

U.S. PATENT DOCUMENTS

| | | | |
|---|---|---|---|
| 2014/0012053 A1* | 1/2014 | Iyer | C10G 9/00 |
| | | | 585/329 |
| 2014/0128485 A1* | 5/2014 | Hassan | B01J 12/007 |
| | | | 422/162 |
| 2017/0137355 A1* | 5/2017 | Sarsani | C07C 29/1518 |
| 2017/0190638 A1* | 7/2017 | Liang | C07C 2/82 |
| 2019/0389788 A1* | 12/2019 | Mamedov | C01B 3/36 |
| 2021/0379549 A1* | 12/2021 | Liu | B01J 8/06 |

* cited by examiner

NON-CATALYTIC OXIDATIVE COUPLING OF METHANE

CROSS-REFERENCE TO RELATED APPLICATIONS

This application claims the benefit of EP 21171121.3 filed Apr. 29, 2021, which is incorporated herein by reference in its entirety for all purposes.

The invention concerns processes for the production of C2+ hydrocarbons from methane ($CH_4$) and oxygen ($O_2$) involving an oxidative coupling of methane reaction.

Oxidative coupling of methane (OCM) is an alternative route for ethylene and propylene production that are currently obtained through steam cracking of higher hydrocarbons.

However, apart from an alternative, OCM could also be an additional route to steam cracking, having in mind that methane ($CH_4$) is a by-product of steam cracking and is typically burnt as fuel for heating the same steam crackers. With the tendency to replace the traditional way of heating with electrical heating, it could be interesting that the $CH_4$ produced in steam cracking units be further used in an OCM unit.

Methane can be used to produce ethane and/or ethylene through the oxidative coupling of the methane (OCM) reaction. While extensive research and development have been devoted to this reaction, the reaction largely remains inefficient on a commercial scale. One of the key challenges is the high reaction temperature (typically greater than 750° C.) required to make the reaction proceed. The need for such a high temperature is due to the bond strength (bond dissociation energy) of the tetrahedral C—H bonds in methane, which is 104 kcal per mole (kcal/mol). This C—H bond strength makes methane less reactive and difficult to undergo oxidative conversion to form ethylene.

The oxidative coupling of the methane is represented by the following equations:

$$2CH_4 + O_2 \rightarrow C_2H_4 + 2H_2O \quad (1)$$

$$2CH_4 + \tfrac{1}{2}O_2 \rightarrow C_2H_6 + H_2O \quad (2)$$

Oxidative conversion of methane to ethylene or ethane is exothermic with $\Delta H = -67.4$ kcal/mol for equation (1) and $\Delta H = -84.6$ kcal/mol for equation (2). Excess heat produced from these reactions can push the conversion of methane to carbon monoxide and carbon dioxide rather than the desired $C_2$ hydrocarbon product:

$$CH_4 + 1.5O_2 \rightarrow CO + 2H_2O \quad (3)$$

$$CH_4 + 2O_2 \rightarrow CO_2 + 2H_2O \quad (4)$$

Indeed for equation (3) $\Delta H = -82.8$ kcal/mol; and for equation (4) $\Delta H = -95.9$ kcal/mol.

It is noted that the heats of reaction for the above equations are given per mole of oxygen consumed.

The excess heat from the reactions in Equations (3) and (4) further exacerbates this situation, thereby substantially reducing the selectivity to ethylene when compared with carbon monoxide and carbon dioxide production.

WO2018146591A1 discloses a method of performing an oxidative coupling of methane reaction to produce C2+ hydrocarbons, the method comprising:

a. preheating a gaseous feed stream to a temperature of at least 400° C., wherein the gaseous feed stream comprises methane ($CH_4$) and oxygen ($O_2$) having an initial $CH_4:O_2$ molar ratio;

b. introducing the preheated gaseous feed stream to an adiabatic reactor, wherein the adiabatic reactor includes a catalyst bed comprising an oxidative coupling of methane catalyst;

c. igniting the oxidative coupling of methane reaction; and d. after igniting the oxidative coupling of methane reaction, incrementally reducing both the temperature and the $CH_4:O_2$ molar ratio of the gaseous feed stream introduced into the adiabatic reactor to an operating inlet temperature of 10° C. to 350° C. and a final $CH_4:O_2$ molar ratio of 9:1 to 3:1 over a startup period such that, at the operating inlet temperature, the oxidative coupling of methane reaction remains ignited and the reactor is in an auto thermal state.

This process is interesting but shows the disadvantage of involving the use of catalysts to perform the OCM reaction. The use of catalysts increases the costs and involves safety problem during the maintenance of the reactors. Also, the selectivity to ethylene is about 25% or less and the selectivity to $CO_2$ is quite high from about 30 to 50%. There is a need to find a solution to lower the $CO_2$ selectivity of the OCM reaction as well as to improve the ethylene selectivity.

WO2018144370A1 discloses a process for producing ethylene and syngas comprising reacting, via OCM, a first reactant mixture ($CH_4$ and $O_2$) in a first reaction zone comprising an OCM catalyst to produce a first product mixture comprising ethylene, ethane, hydrogen, $CO_2$, CO, and unreacted methane; introducing a second reactant mixture comprising the first product mixture to a second reaction zone excluding catalyst to produce a second product mixture comprising ethylene, ethane, hydrogen, CO, $CO_2$, and unreacted methane, wherein a common reactor comprises both the first and second reaction zones, wherein ethane of the second reactant mixture undergoes cracking to ethylene, wherein $CO_2$ of the second reactant mixture undergoes hydrogenation to CO, and wherein an amount of ethylene in the second product mixture is greater than in the first product mixture; recovering a methane stream, an ethane stream, a $CO_2$ stream, an ethylene stream, and a syngas stream (CO and $H_2$) from the second product mixture; and recycling the ethane stream and the carbon dioxide stream to the second reaction zone. This process is interesting but still involves the use of catalysts.

EP0302665 discloses a $C_2$ and higher hydrocarbon product including ethylene to be produced from a methane-containing gaseous paraffinic hydrocarbon feedstock by a process comprising heating the feedstock admixed with oxygen in an amount of at least 5% mol under elevated pressure in a pre-heating zone to a temperature sufficient to cause a spontaneous reaction, the pre-heating and mixing being effected in a manner such that (i) substantial oxygen consumption is avoided, and (ii) a "flash-back" of the reaction to form a diffusion flame at the point of gaseous mixing is prevented, and thereafter in a reaction zone allowing the feedstock mixture to spontaneously react. The process is interesting since it does not involve the use of catalysts. However, it involves high pressure of greater than 20 bar (i.e., greater than 2.0 MPa). The examples show selectivity to $CO_2$ of at most about 15% and selectivity to ethylene of at most 25%. There is still a need to improve the situation.

The present disclosure aims to provide a solution to one or more of the problems encountered in the prior art. In particular, the present disclosure aims to provide a process involving an OCM reaction with an improved balance of selectivity to ethylene and $CO_2$, i.e., wherein the selectivity to ethylene is high and at the same time, the selectivity to $CO_2$ is low. The present disclosure aims to provide a process involving an OCM reaction with an improved balance of selectivity to ethylene and $CO_2$, that is cost-effective.

SUMMARY OF THE DISCLOSURE

One or more of the above needs can be fulfilled by the process according to the present disclosure wherein an oxidative coupling of methane reaction is performed without catalyst and in a counter-current shell-tube reactor.

According to a first aspect, the disclosure provides for a process for a non-catalytic oxidative coupling of methane reaction remarkable in that the process comprises:
- a step of providing a counter-current shell-tube reactor comprising at least two tubes defining a tubular part and a shell part surrounding the tubular part and at least one inlet to feed a gaseous feed stream and at least one outlet to discharge a product stream;
- a step of providing a gaseous feed stream comprising a gas mixture of methane ($CH_4$) and oxygen ($O_2$) in a defined molar ratio and preheated to a defined operating inlet temperature;
- a step of feeding the gaseous feed stream at least in the tubular part or at least in the shell part of the counter-current shell-tube reactor;
- a step of recovering a product stream.

It has been found that it was possible and advantageous to combine feed preheating and reaction in one reactor vessel, employing the heat generated during exothermic OCM. The reactor used is a counter-current shell-tube reactor. Once the reaction has been initiated the heat produced by the OCM reaction is used to preheat the reactor feed from the inlet temperature to a temperature sufficient to perform the non-catalytic OCM reaction.

One of the advantages of the arrangement is that there is a heat exchange between the tube and the shell the moment the gas mixture enters the reactor. The heat exchange from the heat generated by the reaction results in a shorter residence time in the reactor needed for 100% $O_2$ conversion. Also, it was found that such a non-catalytic process wherein the gaseous feed stream is preheated by heat transfer for the reaction mixture allows an increase of the selectivity to ethylene (i.e., the examples show selectivity to ethylene above 35%) whereas, at the same time, the selectivity to $CO_2$ is kept low (i.e., the examples show selectivity to $CO_2$ below 10%).

The process is also advantageous since the operating pressure and temperature can be low. The process of the disclosure with a non-catalytic OCM reaction is advantageous by its low-cost and easy operation, high selectivity to valuable carbon-containing products (CO, $C_2H_4$ and $C_2H_6$), and low amount of $CO_2$ in the product stream. The fact that the reactor operates without catalyst increases the availability of the plant since there are no production losses due to the deactivation of the catalyst with time. Moreover, maintenance operations of a reactor without catalyst are safer (no health risks caused by exposure of the operators to the catalyst dust) and faster.

It is preferred that the reactor dimension and the flow of the gaseous feed stream are selected to have a turbulent flow regime within the reactor.

The tubular part may comprise a single tube or may comprise or a set of two or more tubes.

In a first embodiment, the counter-current shell-tube reactor comprises two inlets and two outlets and the process comprises dividing the gaseous feed stream into two portions defining a first gaseous feed stream portion and a second gaseous feed stream portion, and a step of feeding the first gaseous feed stream portion in the tubular part of the counter-current shell-tube reactor using one inlet and the second gaseous feed stream portion in the shell part of the counter-current shell-tube reactor using the other inlet wherein the second gaseous feed stream portion flows counter-currently relative to the flow direction of the first gaseous feed stream portion. In the said embodiment, as illustrated in FIG. 1, the reactor feed is split into two parts and proceeds counter-currently in two tubes, where the feed preheating and the OCM reaction happen both in the tubular part and shell part of the reactor.

In a second embodiment, the counter-current shell-tube reactor comprises one inlet and one outlet and the process comprises a step of feeding the gaseous feed stream in the tubular part of the counter-current shell-tube reactor using the inlet; wherein a reaction mixture exits the tubular part and continues flowing into the shell part in a counter-currently relative flow direction of the gaseous feed stream in the tubular part. In the said embodiment, as illustrated in FIG. 2, the reactor feed is fed only in the tubular part of the set of tubes; the reaction mixture, in this case, continues flowing from the tubular to the annular side of the reactor.

In a third embodiment, the counter-current shell-tube reactor comprises one inlet and one outlet and the process comprises a step of feeding the gaseous feed stream in the shell part of the counter-current shell-tube reactor using the inlet; wherein a reaction mixture exits the shell part and continues flowing into the tubular part in a counter-currently relative flow direction of the gaseous feed stream in the shell part.

Whatever is the embodiment selected the following features can be used to define the process of the disclosure.

It is preferred that the process further comprises a start-up step of initiating the non-catalytic oxidative coupling of methane reaction; wherein the start-up step comprises providing a gaseous feed stream comprising a gas mixture of methane ($CH_4$) and oxygen ($O_2$) in an initial molar ratio of at least 25.0 wherein the gaseous feed stream is preheated to an initial inlet temperature of at least 650° C.; with preference, of at least 750° C.

For example, in the start-up step, the gaseous feed stream shows an initial molar ratio $CH_4:O_2$ ranging from 25.0 to 150.0; preferably from 27.0 to 100.0; more preferably from 29.0 to 80.0 and even more preferably, from 30.0 to 60.0.

For example, in the start-up step, the gaseous feed stream is preheated to an initial inlet temperature ranging from 650 to 1200° C.; preferably from 700 to 1100° C.; more preferably from 750 to 1100° C. or from 750 to 1050° C. and even more preferably, from 800 to 1000° C.

For example, the process comprises preheating the gaseous feed stream to an operating inlet temperature of at least 10° C.; preferably to an operating inlet temperature of at least 40° C.

For example, the process comprises preheating the gaseous feed stream to an operating inlet temperature ranging from 30 to 550° C.; for example, from 40 to 520° C.

For example, the gaseous feed stream shows an operating molar ratio $CH_4:O_2$ of at least 7.0; preferably at least 7.5, more preferably at least 8.0, even more preferably at least 8.5 and most preferably at least 9.0.

For example, the gaseous feed stream further comprises one or more hydrocarbons different from methane; with preference, the gaseous feed stream further comprises ethane.

For example, the gaseous feed stream shows an operating molar ratio $CH_4:O_2$ ranging from 7.0 to 20.0; preferably, from 8.0 to 18.0; more preferably from 8.5 to 15.0 and even more preferably from 9.0 to 14.0.

For example, the ratio of the volume (V) of the reactor divided by the flow rate ($F_{CH4,0}$) of methane in the feed stream (i.e. $V/F_{CH4,0}$) is at least $0.002$ m$^3$s mol$^{-1}$; preferably at least $0.005$ m$^3$s mol$^{-1}$ or at least $0.008$ m$^3$s mol$^{-1}$.

For example, the ratio of the volume (V) of the reactor divided by the flow rate ($F_{CH4,0}$) of methane in the feed stream (i.e. $V/F_{CH4,0}$) is at most m$^3$s mol$^{-1}$.

For example, the process comprises an operating pressure in the reactor ranging from 0.2 to 5.0 MPa; preferably from 0.3 to 3.5 MPa; more preferably from 0.4 to 1.8 MPa.

For example, the product stream comprises ethylene ($C_2H_4$) and ethane ($C_2H_6$) wherein the molar ratio $C_2H_4:C_2H_6$ is above 3.0; with preference ranging from 3:1 to 8.0.

For example, the product stream comprises ethylene ($C_2H_4$) and carbon dioxide ($CO_2$) wherein the molar ratio $C_2H_4:CO_2$ is above 3.0.

For example, the length and diameter tubular part of the reactor is selected to have a Reynold number in the tubular part is equal to or greater than 10,000 in each of the one or more tube of the tubular part.

In a preferred embodiment, the gaseous feed stream shows an operating molar ratio $CH_4:O_2$ ranging from 8.0 to 14.0; and an operating inlet temperature ranging from 200 to 550° C. Such a combination of parameters allows achieving a further improved balance selectivity to ethylene and $CO_2$. With preference, the operating pressure in the reactor is ranging from 0.6 to 1.0 MPa. This further increases the production rate. With preference, the operating inlet temperature is ranging from 350 to 550° C. This further decrease the selectivity to $CO_2$.

In a preferred embodiment, the gaseous feed stream shows an operating inlet temperature ranging from 30° C. to 300° C. and an operating pressure in the reactor ranging from 0.5 to 1.8 MPa or from 0.5 to 0.9 MPa; with preference, the operating inlet temperature ranging from 30° C. to below 200° C. The selection of a low operating inlet temperature range allows for increasing the methane conversion rate. With preference, the gaseous feed stream shows an operating molar ratio $CH_4:O_2$ ranging from 7.0 to 9.5. The combination of the defined operating inlet temperature range together with the operating molar ratio $CH_4:O_2$ range provides an improvement in the ethylene production rate.

In a preferred embodiment, the gaseous feed stream shows an operating inlet temperature ranging from 30° C. to 200° C., an operating pressure in the reactor ranging from 0.3 to 0.8 MPa; and the gaseous feed stream shows an operating molar ratio $CH_4:O_2$ ranging from 7.0 to 9.0. The defined combination of parameter provides an improved balance between the ethylene production rate, the ethylene selectivity and the methane conversion, while at the same time the $CO_2$ selectivity is kept low.

According to a second aspect, the disclosure provides for a method comprising providing the product stream recovered in the process according to the first aspect and performing a reaction selected from a hydroformylation and a synthesis gas fermentation.

With preference, the product stream comprising carbon dioxide and one or more olefins; the method is devoid of a step of separation of the carbon dioxide from the one or more olefins before performing a reaction selected from a hydroformylation and a synthesis gas fermentation.

DETAILED DESCRIPTION

For the disclosure, the following definitions are given:

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4, 5 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

The particular features, structures, characteristics or embodiments may be combined in any suitable manner, as would be apparent to a person skilled in the art from this disclosure, in one or more embodiments.

The process according to the present disclosure wherein an oxidative coupling of methane reaction is performed without catalyst and in a counter-current shell-tube reactor. It is preferred that the reactor dimension and the flow of the gaseous feed stream are selected to have a turbulent flow regime within the reactor.

Figure 1:
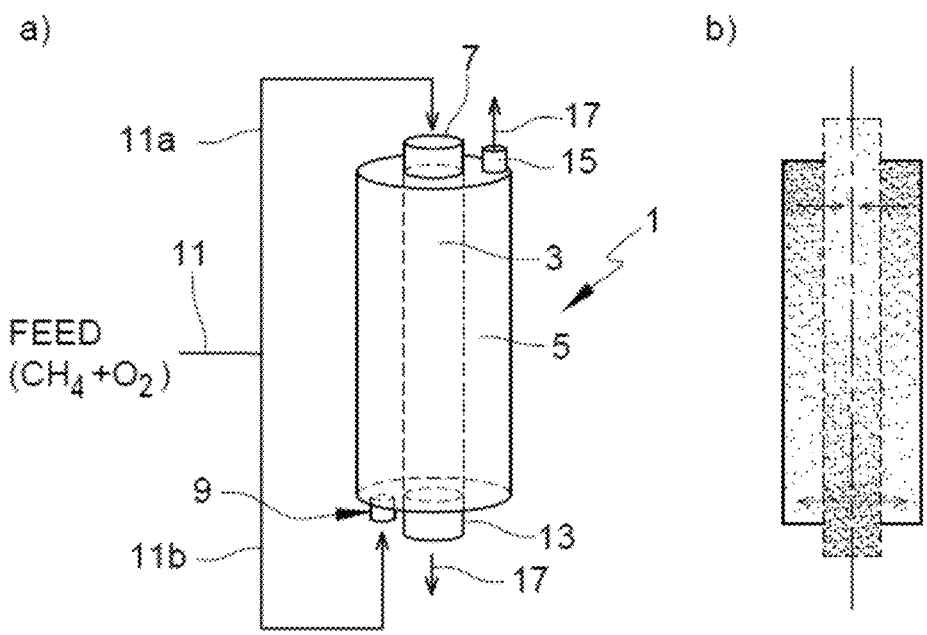
FIG. 1: Schematics of the countercurrent shell-tube reactor according to the first arrangement wherein the gaseous feed stream is fed into both tubular part and shell part; (a) arrangement of the reactor (b) temperature exchange.
Figure 2:
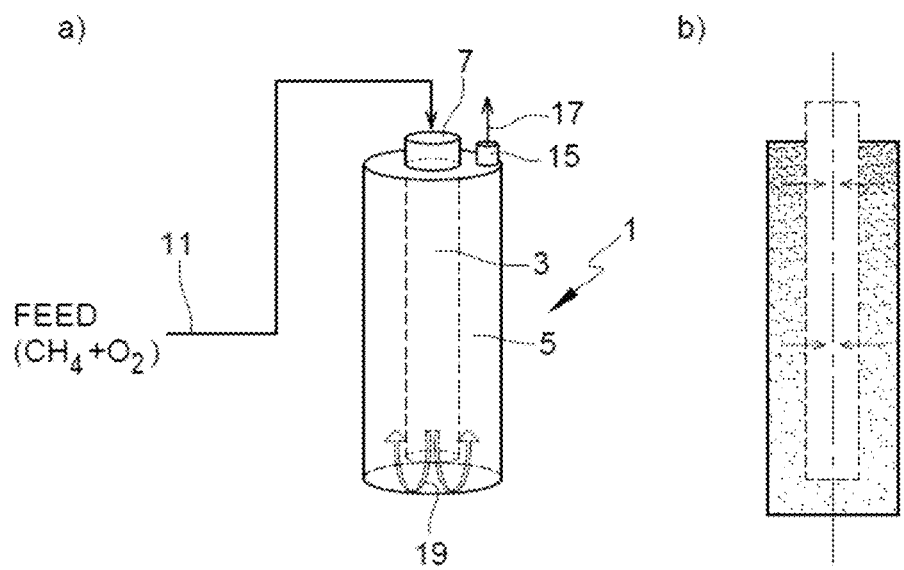
FIG. 2: Schematics of the countercurrent shell-tube reactor according to the second arrangement wherein the gaseous feed stream gas mixture is fed into the tubular part and leaves the reactor by the shell part; (a) arrangement of the reactor (b) temperature exchange.

Reference is made to FIGS. 1 and 2 that show a counter-current shell-tube reactor 1 comprising at least two tubes (3, 5) defining a tubular part 3 and a shell part 5 surrounding the tubular part 3. The disclosure provides a process for a non-catalytic oxidative coupling of methane reaction remarkable in that the process comprises:

- a step of providing a counter-current shell-tube reactor 1 comprising at least two tubes (3, 5) defining a tubular part 3 and a shell part 5 surrounding the tubular part 3 and at least one inlet (7, 9) to feed a gaseous feed stream 11 and at least one outlet (13, 15) to discharge a product stream 17;
- a step of providing a gaseous feed stream 11 comprising a gas mixture of methane ($CH_4$) and oxygen ($O_2$) in a defined molar ratio and preheated to a defined operating inlet temperature;
- a step of feeding the gaseous feed stream 11 at least in the tubular part 3 or at least in the shell part 15 of the counter-current shell-tube reactor 1;
- a step of recovering a product stream 17.

The tubular part may comprise a single tube or may comprise or a set of two or more tubes.

The First Arrangement

In a first embodiment illustrated in FIG. 1 (i.e. the first arrangement), the counter-current shell-tube reactor 1 comprises two inlets (7, 9) and two outlets (13, 15) and the process comprises dividing the gaseous feed stream 11 into two portions (11*a*, 11*b*) defining a first gaseous feed stream portion 11*a* and a second gaseous feed stream portion 11*b*; and a step of feeding the first gaseous feed stream portion 11*a* in the tubular part 3 of the counter-current shell-tube reactor 1 using one inlet 7 and the second gaseous feed stream portion 11*b* in the shell part 5 of the counter-current shell-tube reactor using the other inlet 9; wherein the second gaseous feed stream portion 11*b* flows counter-currently relative to the flow direction of the first gaseous feed stream portion 11*a*. In the said embodiment, the gaseous feed stream 11 is split into two portions (11*a*, 11*b*) and proceeds counter-currently in two tubes (3, 5). The preheating of the feed stream and the OCM reaction happen both in the tubular and shell parts (3, 5) of reactor 1. The heat generated by the OCM reaction on the first gaseous feed stream portion 11*a* in the tubular part 3 is transferred to the second gaseous feed stream portion 11*b* in the shell part 5 for preheating and vice-versa. The concentration and temperature profiles along the reactor length are symmetrical in the tube and the shell for the first arrangement. The product stream 17 exits the reactor by the two outlets (13,15).

For the first arrangement, the dimension of the reactor and the flow rate are selected so that the position where the OCM reaction takes place (in both the tube and the shell part) is preferentially in the middle of the reactor to allow for sufficient residence time of the fluid for the preheating of the cold reactants. For example, the length of the reactor (L) is at least 3 m, the internal diameter of the tubular part (Dt) is at least 80 mm, the wall thickness between the tubular part and the shell part is about 2 mm and the internal diameter of the shell part (Ds) is at least 80 mm; in such conditions, the reciprocal flow speed or residence time of the gaseous feed stream is at least 0.09 $m^3 s\ mol^{-1}$. The diameter of the shell is selected to have an open cross-sectional area available for the passage of the fluid in the shell that is between 80 to 120% of the open cross-sectional area of the tube (similar linear velocities within the 80-120% range).

An optional embodiment of the present configuration is one shell envelope with multiple tubes where the open sectional area of the shell is between 80 and 120% of the sum of the sectional areas of all tubes. The multiple tubes are typically fixed onto two plates or sheets, one on the inlet and one at the outlet. A tube sheet is usually made from a round flat piece of plate sheet with holes drilled to accept the tubes to support and isolate tubes in heat exchanger configuration. Hence the feed is homogeneously distribution over the multiple tubes while the shell side is fed laterally or via a connected inlet pipe passing through the tube sheet from the other side of the reactor. The first portion of the feed is fed via the inlet of the tube sheet and leaving the tubes via the tube sheet on the opposite side of the reactor. The other portion of the feed is fed to the shell side counter-currently to the flow in the tube side and leaves the shell side on the opposite side. The diameter of the shell is selected to have an open cross-sectional area available for the passage of the fluid in the shell that is between 80 to 120% of the sum of open cross-sectional areas of all the tubes (similar linear velocities within the 80-120% range).

The Second Arrangement

In a second embodiment illustrated in FIG. 2 (i.e. the second arrangement), the counter-current shell-tube reactor 1 comprises one inlet 7 and one outlet 15 and the process comprises a step of feeding the gaseous feed stream 11 in the tubular part 3 of the counter-current shell-tube reactor 1 using the inlet 7; wherein a reaction mixture 19 exits the tubular part 3 and continues flowing into the shell part 5 counter-currently relative to the flow direction of the gaseous feed stream 11 in the tubular part 3. In the said embodiment, the gaseous feed stream 11 is only in the tubular part 3 of the set of tubes; the reaction mixture, in this case, continues flowing from the tubular part to the shell part of the reactor. The heat generated by the OCM reaction is transferred from the shell part 5 to the tubular part 3 for preheating the gaseous feed stream 11.

For the second arrangement, the dimension of the reactor and the flow rate are selected so that the position where the OCM reaction takes place is preferentially in the shell part of the reactor to allow for sufficient residence time of the fluid for the preheating of the cold reactants. For example, the length of the reactor (L) is at least 3 m, the internal diameter of the tubular part (Dt) is at least 40 mm, the wall thickness between the tubular part and the shell part is about 2 mm and the internal diameter of the shell part (Ds) is at least 60 mm; in such conditions, the reciprocal flow speed or residence time of the gaseous feed stream is at least 0.0225 $m^3 s\ mol^{-1}$. The diameter of the shell is selected to have an open cross-sectional area available for the passage of the fluid in the shell that is between 50 to 150% of the sum of open cross-sectional areas of the tube (similar linear velocities within the 50-150% range).

An optional embodiment of the present configuration is one shell envelope with multiple tubes where the open sectional area of the shell is between 50 and 150% of the sum of the sectional areas of all tubes. The multiple tubes are typically fixed onto one plate or sheet. A tube sheet is usually made from a round flat piece of plate sheet with holes drilled to accept the tubes to support and isolate tubes in heat exchanger configuration. Hence the feed is homogeneously distribution over the multiple tubes while at the end of the tubes the feed stream turns into the shell side. In one embodiment the feed is fed via the inlet of the tube sheet and leaving the shell side of the reactor. In another embodiment, the feed is fed to the shell side and leaving the reactor via the tube sheet. The diameter of the shell is selected to have an open cross-sectional area available for the passage of the fluid in the shell that is between 50 to 150% of the sum of open cross-sectional areas of all the tubes (similar linear velocities within the 50-150% range).

The Third Arrangement

Figure 3:
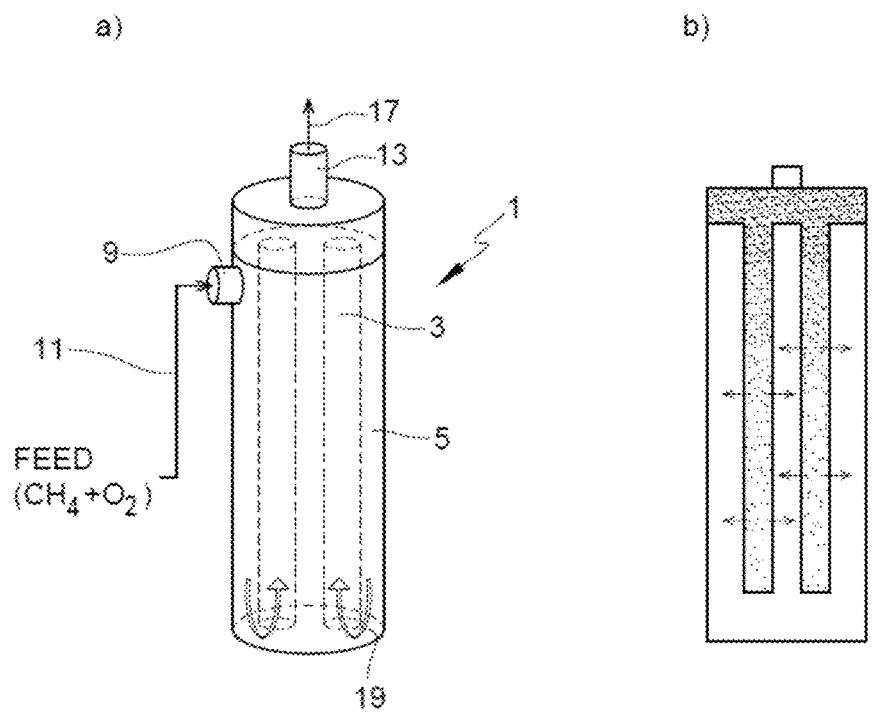
FIG. 3: Schematics of the countercurrent shell-tube reactor according to the third arrangement wherein the gaseous feed stream gas mixture is fed into the shell part and leaves the reactor by the tubular part; (a) arrangement of the reactor (b) temperature exchange.

In a third embodiment illustrated in FIG. 3 (i.e. the third arrangement), the counter-current shell-tube reactor 1 comprises one inlet 9 and one outlet 13 and the process comprises a step of feeding the gaseous feed stream 11 in the shell part 5 of the counter-current shell-tube reactor 1 using the inlet 9; wherein a reaction mixture 19 exits the shell part 5 and continues flowing into the tubular part 3 counter-currently relative to the flow direction of the gaseous feed stream 11 in the shell part 5. In the said embodiment, the gaseous feed stream 11 is only fed in the shell part 5; the reaction mixture 19, in this case, continues flowing from the shell part to the tubular part of the reactor. The heat generated by the OCM reaction is transferred from the tubular part 3 to the shell part 5 for preheating the gaseous feed stream 11.

In FIG. 3, one shell envelope with multiple tubes (such as two tubes) where the open sectional area of the shell is between 80 and 120% of the sum of the sectional areas of all tubes. However, the use of a tubular part comprising a ingle tube is also possible.

The below description can be used whatever is the arrangement selected unless specific indication to the contrary.

Selection of the Reactor and the Flow Conditions

As it can be understood from the above, the countercurrent shell-tube reactor 1 is selected to have a cross-sectional area ratio between the tubular part and the shell part of about 0.8:1.2; preferably of about 0.9:1.1; more preferably of about 1.0:1.0. For example, the cross-sectional area of the tubular part and the shell part is the same.

Also, the linear velocity of the flow between the tubular part and the shell part of about 0.8:1.2; preferably of about 0.9:1.1; more preferably of about 1.0:1.0. For example, the linear velocity of the flow within the tubular part and the shell part is the same.

For example, the reactor is selected to have a tubular part with an internal diameter (Dt) of at least 40 mm, a wall thickness between the tubular part and the shell part is about 2 mm and the shell part an internal diameter (Ds) of at least 80 mm; wherein the cross-sectional area ratio between the tubular part and the shell part of about 0.8:1.2. With the said dimensions the length of the reactor is at least 3 m if the reactor comprises 2 inlets and at least 4 m if the reactor comprises 1 inlet.

For example, the length and diameter tubular part of the reactor is selected to have a Reynold number (Re) in each of the one or more tubes of the tubular part equal to or greater than 10,000. Re 10 000, where $Re=u_f D_H \rho_f/\mu_f$, with $u_f$ being the velocity of the fluid, $\rho_f$ density of the fluid, $\mu_f$ dynamic viscosity of the fluid, and $D_H$ hydraulic diameter of the tube ($D_H$ is equal to the inner tube diameter) or shell ($D_H$ is equal to the inner shell diameter–outer tube diameter).

The Preheating of the Gaseous Feed Stream to an Inlet Temperature.

The preheating can be done by any means. In an embodiment, preheating can be done by heat exchange between the hot reactor outlet and the cold feed or by a furnace heater (either fuel combustion heated, steam fed heat exchanger or electrical heater).

The Start-Up Step of Initiating the Non-Catalytic Oxidative Coupling of Methane Reaction To initiate the exothermic reaction at the start can be done by over preheating the feed with eventually increased methane to oxygen ratio and/or by spark ignition or plasma activation of the preheated feed. The spark ignition or plasma activation can be done at any location in the reactor.

It is preferred that the process further comprises a start-up step of initiating the non-catalytic oxidative coupling of methane reaction; wherein the start-up step comprises providing a gaseous feed stream comprising a gas mixture of methane ($CH_4$) and oxygen ($O_2$) in an initial molar ratio of at least 25.0 wherein the gaseous feed stream is preheated to an initial inlet temperature of at least 650° C.; with preference of at least 750° C.

For example, in the start-up step, the gaseous feed stream shows an initial molar ratio $CH_4:O_2$ of at least 25.0; preferably, at least 27.0; more preferably, at least 29.0 and even more preferably, at least 30.0.

For example, in the start-up step, the gaseous feed stream shows an initial molar ratio $CH_4:O_2$ ranging from 25.0 to 100.0; preferably from 27.0 to 80.0; more preferably from 28.0 to 50.0; even more preferably from 29.0 to 40.0.

For example, in the start-up step, the gaseous feed stream shows an initial molar ratio $CH_4:O_2$ of at least 680° C.; preferably, at least 700° C.; more preferably, at least 750° C. and even more preferably, at least 800° C.

For example, in the start-up step, the gaseous feed stream is preheated to an initial inlet temperature ranging from 650 to 1200° C.; preferably from 700 to 1100° C.; more preferably from 750 to 1050° C. and even more preferably, from 800 to 1000° C.

For example, in the start-up step, the pressure in the reactor of at least 0.1 MPa; preferably at least 0.2 MPa; more preferably at least 0.3 MPa and even more preferably at least 0.4 MPa. In some embodiments, the pressure in the reactor of at least 0.5 MPa of at least 0.6 MPa or at least 0.7 MPa.

For example, in the start-up step, the pressure in the reactor of at most 2.0 MPa; preferably at most 1.8 MPa; more preferably at most 1.5 MPa and even more preferably at most 1.2 MPa or at most 1.0 MPa. In some embodiments, the pressure in the reactor of at most 0.9 MPa of at most 0.8 MPa or at most 0.6 MPa.

For example, in the start-up step, the pressure in the reactor ranging from 0.1 to 2.0 MPa; preferably from 0.2 to 1.8 MPa; more preferably from 0.3 to 1.5 MPa.

Once the exothermic reaction is initiated, the methane to oxygen ration can be slowly reduced while the preheating of the feed is reduced and the operating pressure adjusted to the desired value.

The Operating Conditions

Once the OCM reaction is initiated the process comprises reducing both the inlet temperature and the molar methane to oxygen ratio. The inlet temperature is reduced from the initial inlet temperature to the operating inlet temperature. For example, the inlet temperature reduction is at least 100° C.; preferably at least 150° C.; more preferably at least 200° C. In some cases, the inlet temperature is reduced to at least 300° C. or at least 400° C. or at least 500° C. or at least 600° C. The reduction of the inlet operating temperature allows a reduction in the costs.

For example, the process comprises preheating the gaseous feed stream to an operating inlet temperature of at least 10° C.; preferably, at least 20° C.; more preferably, at least 30° C.; even more preferably, at least 40° C. In some embodiments, the operating inlet temperature is at least 200° C. or at least 250° C. or at least 300° C. or at least 350° C.

For example, the process comprises preheating the gaseous feed stream to an operating inlet temperature of at most 550° C.; preferably, at most 520° C. In some embodiments, the operating inlet temperature is at most 300° C. or at most 250° C. or at most 200° C.

For example, the process comprises preheating the gaseous feed stream to an operating inlet temperature ranging from 10 to 550° C.; for example, from 30 to 550° C.; for example, from 40 to 520° C. In some embodiments, wherein the selectivity to ethylene is to be favoured or the selectivity to $CO_2$ is to be kept as low as possible, the operating inlet temperature is ranging from 200 to 550° C., or from 350 to 550° C. In some embodiments, wherein the production rate of ethylene or the methane conversion rate is to be favoured, the operating inlet temperature is ranging from 10 to 300° C., or from 30 to 200° C.

The molar ratio $CH_4:O_2$ is reduced from the initial molar ratio $CH_4:O_2$ to the operating molar ratio $CH_4:O_2$. For example, the initial molar ratio $CH_4:O_2$ is divided by at least 1.2, preferably by at least 1.3 or at least 1.5. In some embodiments, the initial molar ratio $CH_4:O_2$ is divided by at least 2.0; preferably, at least 2.5; more preferably at least 3.0. The reduction of the molar ratio $CH_4:O_2$, i.e., the increase of the oxygen concentration in the gaseous feed stream, allows an increase of the selectivity to $C_2+$.

For example, the gaseous feed stream shows an operating molar ratio $CH_4:O_2$ of at least 7.0; preferably at least 7.5, more preferably at least 8.0, even more preferably at least 8.5 and most preferably at least 9.0.

For example, the gaseous feed stream shows an operating molar ratio $CH_4:O_2$ of at most 20.0; preferably at most 18.0, more preferably at most 15.0, and even more preferably at most 14.0. In some embodiments, the gaseous feed stream shows an operating molar ratio $CH_4:O_2$ of at most 10.0, or at most 9.5 or at most 9.0 or at most 8.5.

For example, the gaseous feed stream shows an operating molar ratio $CH_4:O_2$ ranging from 7.0 to 20.0; preferably, from 8.0 to 18.0; more preferably from 8.5 to 15.0 and even more preferably from 9.0 to 14.0. In some embodiments the operating molar ratio $CH_4:O_2$ ranging from 7.0 to 9.5 or from 7.0 to 9.0.

For example, the gaseous feed stream further comprises one or more hydrocarbons different from methane; with preference, the gaseous feed stream further comprises ethane.

It is preferred that the ratio of the volume (V) of the reactor divided by the flow rate ($F_{CH4,0}$) of methane in the feed stream (i.e. $V/F_{CH4,0}$) is at most 0.1 $m^3 s\ mol^{-1}$.

For example, the ratio of the volume (V) of the reactor divided by the flow rate ($F_{CH4,0}$) of methane in the feed stream (i.e. $V/F_{CH4,0}$) is at least 0.002 $m^3 s\ mol^{-1}$; preferably at least 0.005 $m^3 s\ mol^{-1}$ or at least 0.008 $m^3 s\ mol^{-1}$. For example, the process comprises an operating pressure in the reactor of at least 0.1 MPa; preferably at least 0.2 MPa; more preferably at least 0.3 MPa and even more preferably at least 0.4 MPa. In some embodiments, the operating pressure in the reactor of at least 0.5 MPa of at least 0.6 MPa or at least 0.7 MPa.

For example, the process comprises an operating pressure in the reactor of at most 5.0 MPa; preferably at most 4.0 MPa or at most 3.5 MPa; more preferably at most 3.0 MPa and even more preferably at most 2.5 MPa; most preferably of at most 2.0 MPa or at most 1.0 MPa. In some embodiments, the operating pressure in the reactor of at most 0.9 MPa of at most 0.8 MPa or at most 0.6 MPa.

For example, the process comprises an operating pressure in the reactor ranging from 0.1 to 2.0 MPa, or from 0.2 to 1.8 MPa, or from 0.2 to 1.0 MPa, or from 0.3 to 1.5 MPa, or from 0.3 to 0.9 MPa, or from 0.4 to 0.8 MPa.

The Product Stream

The process of the disclosure allows a selectivity to ethylene of about 30% or more; preferably of about 32% or more. In some embodiments, the selectivity to ethylene of about 35% or more; preferably of about 39% or more or about 40% or more.

The selectivity to ethylene can be compared to the selectivity to ethane resulting in a high molar ratio $C_2H_4:C_2H_6$. For example, the product stream comprising ethylene ($C_2H_4$) and ethane ($C_2H_6$) wherein the molar ratio $C_2H_4:C_2H_6$ is above 3.0; preferably, above 3.1 or above 3.5. In some cases, the molar ratio $C_2H_4:C_2H_6$ is above 4.0 or above 4.5.

For example, the product stream comprising ethylene ($C_2H_4$) and ethane ($C_2H_6$) wherein the molar ratio $C_2H_4:C_2H_6$ is ranging from 3.0 to 10.0; preferably from 3:1 to 8.0; more preferably from 3.5 to 6.0.

The selectivity to ethylene can be compared to the selectivity of carbon dioxide resulting in a high molar ratio $C_2H_4:CO_2$. For example, the process comprises a step of recovering a product stream comprising ethylene ($C_2H_4$) and carbon dioxide ($CO_2$) wherein the molar ratio $C_2H_4:CO_2$ is above 3.0; preferably, above 3.1 or above 3.5. In some cases, the molar ratio $C_2H_4:C_2H_6$ is above 4.0 or above 4.5.

Without being bound to a theory, it is believed that one of the reasons for the high selectivity to ethylene achieved by the process of the present disclosure is a good rate of conversion of the acetylene to ethylene due to the heat transfer between the tubular and the shell part of the reactor. As shown in the examples, the selectivity to acetylene ($C_2H_2$) is low. For example, the selectivity to acetylene is at most 5.0%; preferably at most 4.5%. In some embodiments, the selectivity to acetylene is at most 3.0%; preferably at most 2.5%; more preferably at most 2.0%; even more preferably at most 1.5%; and most preferably at most 1.0%.

Also, the process according to the disclosure allows propylene to be produced. The selectivity to propylene is preferably at least 3.0%. In some embodiments, the selectivity to propylene can be from 3.0 to 15.0%: preferably from 3.0 to 12.0%; more preferably from 3.0 to 10.0%.

The different parameters for operating conditions can be combined upon the desired balance of selectivity and/or conversion rate and/or production rate. Non-limitative combinations of parameters are provided below as preferred embodiments.

In a preferred embodiment, the gaseous feed stream shows an operating molar ratio $CH_4:O_2$ ranging from 8.0 to 14.0; and an operating inlet temperature ranging from 200 to 550° C. Such a combination of parameters allows achieving a further improved balance selectivity to ethylene and $CO_2$. With preference, the operating pressure in the reactor is ranging from 0.6 to 1.0 MPa. This further increases the production rate. With preference, the operating inlet temperature is ranging from 350 to 550° C. This further decreases the selectivity to $CO_2$.

In a preferred embodiment, the gaseous feed stream shows an operating inlet temperature ranging from 30° C. to 300° C. and operating pressure in the reactor ranging from 0.5 to 0.9 MPa; with preference, the operating inlet temperature is ranging from 30° C. to below 200° C. The selection of a low operating inlet temperature range allows for increasing the methane conversion rate. With preference, the gaseous feed stream shows an operating molar ratio $CH_4:O_2$ ranging from 7.0 to 9.5. The combination of the defined operating inlet temperature range together with the operating molar ratio $CH_4:O_2$ range provides an improvement in the ethylene production rate.

In a preferred embodiment, the gaseous feed stream shows an operating inlet temperature ranging from 30° C. to 200° C., an operating pressure in the reactor ranging from 0.3 to 0.8 MPa; and the gaseous feed stream shows an operating molar ratio $CH_4:O_2$ ranging from 7.0 to 9.0.

The defined combination of parameter provides an improved balance between the ethylene production rate, the ethylene selectivity and the methane conversion, while at the same time the $CO_2$ selectivity is kept low.

The effluent of the non-catalytic OCM reactor consist mainly of ethylene, ethane, carbon monoxide and hydrogen. This mixture can after cooling be further converted without further separation to useful products, either coupling the syngas onto the ethylene in order to make C3 compounds or fermentation of the cooled mixture without further separation during which essentially the syngas is converted into C2 or C4 oxygenates, like ethanol and butanol.

Hydroformylation, also known as oxo synthesis, is an industrial process to produce aldehydes from alkenes. The process entails treatment of an alkene typically with high pressures (between 10 and 100 atmospheres) of carbon monoxide and hydrogen at temperatures between 40 and 200° C. Transition metal catalysts are required. Industrial processes based on cobalt catalysts are mainly used for the production of medium- to long-chain olefins, whereas the rhodium-based catalysts are usually used for the hydroformylation.

$$H_2 + CO + CH_2=CH_2 \rightarrow CH_3CH_2CHO$$

Ethylene can also be converted directly into propanol by reductive hydroformylation according to the following reaction:

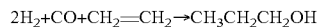
$$2H_2 + CO + CH_2=CH_2 \rightarrow CH_3CH_2CH_2OH$$

Synthesis gas fermentation, is a microbial process. In this process, a mixture of hydrogen, carbon monoxide, and carbon dioxide, known as syngas, is used as carbon and energy sources, and then converted into fuel and chemicals by microorganisms.

The main products of syngas fermentation include ethanol, butanol, acetic acid and butyric acid. These microorganisms are mostly known as acetogens including *Clostridium Uungdahlii, Clostridium autoethanogenum, Eubacterium limosum, Clostridium carboxidivorans* P7, *Peptostreptococcus* productus, and *Butyribacterium methylotrophicum*. Most use the Wood-Ljungdahl pathway.

Syngas fermentation process has advantages over a chemical process since it takes places at lower temperature and pressure, has higher reaction specificity, tolerates higher amounts of sulfur compounds, and does not require a specific ratio of CO to $H_2$.

$$4H_2 + 2CO \rightarrow CH_3CH_2OH + H_2O$$

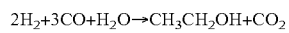
$$2H_2 + 3CO + H_2O \rightarrow CH_3CH_2OH + CO_2$$

$$6CO + 3H_2O \rightarrow CH_3CH_2OH + 4CO_2$$

EXAMPLES

The following non-limiting examples based on reactor simulations carried out with Matlab 2017 and gPROMS 1.3.1 illustrate the disclosure. The simulation was made with a gaseous feed stream consisting in a gas mixture of methane ($CH_4$) and oxygen ($O_2$).

Example 1 (Comparative)

The pressure of P=4 bar (0.4 MPa) was taken as the base case conditions, and the simulations were carried out for three different inlet temperatures: 500° C., 600° C., and 650° C. with an inlet feed ratio $[CH_4/O_2]_0$ of 10 mol/mol. At 100% $O_2$ conversion, the information about the space-time, conversion, selectivity and adiabatic temperature rise are shown in Table 1.

$V/F_{CH4,0}$ (m³s mol⁻¹) is the volume (V) of the reactor divided by the flow rate ($F_{CH4,0}$) of methane in the feed stream.

TABLE 1

Results of adiabatic simulations at 100% $O_2$ conversion for different inlet temperatures. (Reaction conditions: P = 0.4 MPa)

| | Adiabatic simulation | | | | | Isothermal simulation |
|---|---|---|---|---|---|---|
| $[CH_4/O_2]_0$, mol mol⁻¹ | 10 | 10 | 10 | 8.0 | 7.0 | 10 |
| $T_0$, °C. | 650 | 600 | 500 | 500 | 500 | 876* |
| $V/F_{CH4,0}$, m³s mol⁻¹ | 0.075 | 0.233 | 4.080 | 3.29 | 2.95 | 0.02 |
| $X(CH_4)$, % | 14.9 | 14.3 | 13.0 | 16.4 | 18.0 | 15.3 |
| $S(C_2H_4)$, % | 34.0 | 35.0 | 35.1 | 31.0 | 27.0 | 41.3 |
| $S(CO)$, % | 36.9 | 38.5 | 42.4 | 41.6 | 43.4 | 36.6 |
| $S(C_2H_6)$, % | 1.2 | 1.5 | 2.3 | 1.2 | 0.7 | 5.8 |
| $S(C_2H_2)$, % | 15.7 | 12.1 | 6.4 | 13.0 | 17.7 | 5.1 |
| $S(CO_2)$, % | 3.0 | 3.2 | 3.5 | 4.3 | 4.9 | 3.0 |
| $\Delta T$, °C. | 308 | 331 | 376 | 444 | 490 | n.a. |

*temperature is chosen the same as outlet T for the adiabatic reactor simulation at $T_0$ = 500° C.

The most favourable operation with regards to the selectivity is the one at the inlet temperature of 500° C. since the outlet temperature (500+376=876° C.) is not high enough to result in a higher degree of acetylene production. However, this comes at a cost of higher residence time in the reactor to obtain 100% $O_2$ conversion, i.e., the reactor with the inlet feed temperature of 500° C. is 4.080/0.075=54 times bigger in volume than the reactor with the inlet feed temperature of 650° C. (for the same inlet flowrates).

For the sake of operation comparison of an adiabatic and isothermal reactor, an additional isothermal simulation was carried out at T=876° C. (outlet temperature of the adiabatic reactor, case inlet $T_0$=500° C.). The results show that running an isothermal reactor is more profitable (4.08/0.02=204 times smaller reactor), with somewhat better (but quite comparable) conversion and selectivity to the desired product ($C_2H_4$ and $C_2H_6$). In an adiabatic reactor, the bigger portion of the reactor is used to warm up the reaction mixture to the temperature where the reaction kinetics becomes faster. However, the isothermal reactor for OCM is experimentally more difficult to operate, if not unfeasible, compared to the adiabatic reactor.

To see if the reaction can be carried out adiabatically at the reactor feed temperature of 500° C., but in a smaller reactor volume, additional simulations were carried out at $T_0$=500° C., lowering the inlet feed ratio $[CH_4/O_2]_0$. The results for $[CH_4/O_2]_0$=7 and 8 mol/mol are also reported in table 1. If the inlet feed ratio is changed from 10 mol/mol to 7 mol/mol, the reactor size can decrease by some 30% for the same flow rates; however, at a cost of worse selectivity.

Example 2—First Arrangement

The model used for simulation can be used in the case of a fully developed turbulent flow. If the tube is kept with a smaller diameter (around 2 mm), the velocity should be high to result in a fully turbulent flow. However, due to that, the reactor tube would need to be very long to result in 100% $O_2$ conversion. Therefore, a compromise was made, and the inner diameter of the tube, Dt, was fixed to 80 mm in all the calculations. The wall thickness between the tube and shell was kept at 2 mm, and the (inner) shell diameter was 116 mm. This diameter of the shell was chosen to have the same cross-sectional area available for the passage of the fluid in both the shell and the tube (same linear velocities). The length of the reactor in the first arrangement was fixed at 20 m, whereas in the second arrangement, it was 10 m. The shell was assumed as perfectly insulated.

The start-up step (i.e. the start-up procedure for reactor) was performed under the same conditions except or 0.8 MPa upon the cases (the initial pressure is the same as the operating pressure).

The start-up step was conducted under the following conditions
For cases with a pressure of P=0.4 MPa
[$CH_4/O_2$]$_0$=30.0 mol mol-$^1$
$F_0(CH_4)$=4.0 kmol h$^{-1}$
$T_0$=750° C.
For cases with a pressure of P=0.8 MPa
[$CH_4/O_2$]$_0$=30.0 mol mol$^{-1}$
$F_0(CH_4)$=16.0 kmol h$^{-1}$
$T_0$=750° C.

Figure 4:
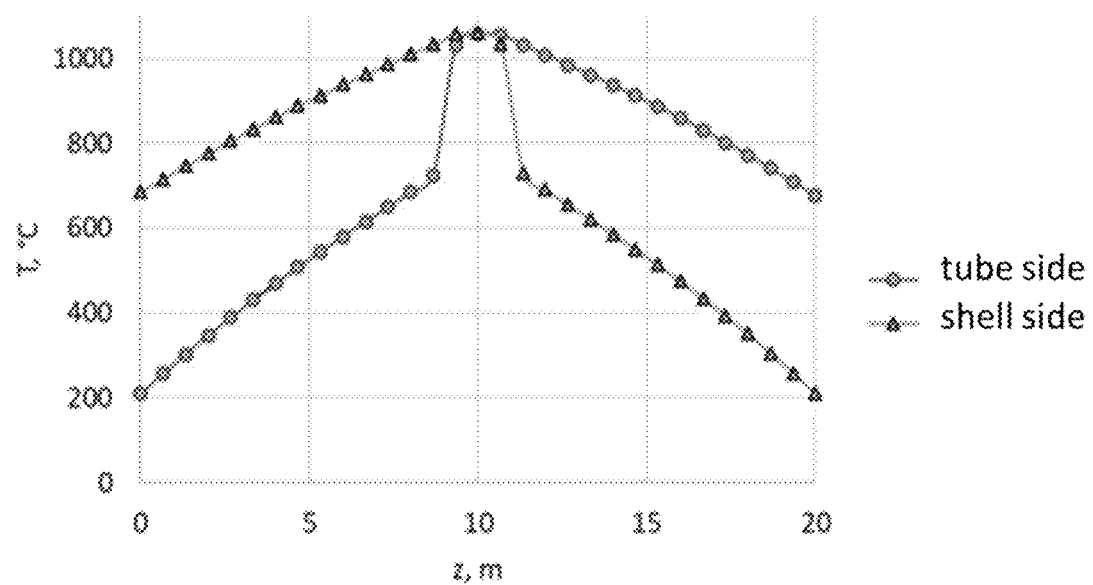
FIG. 4: symmetrical temperature profile in tube and shell.
Figure 5:
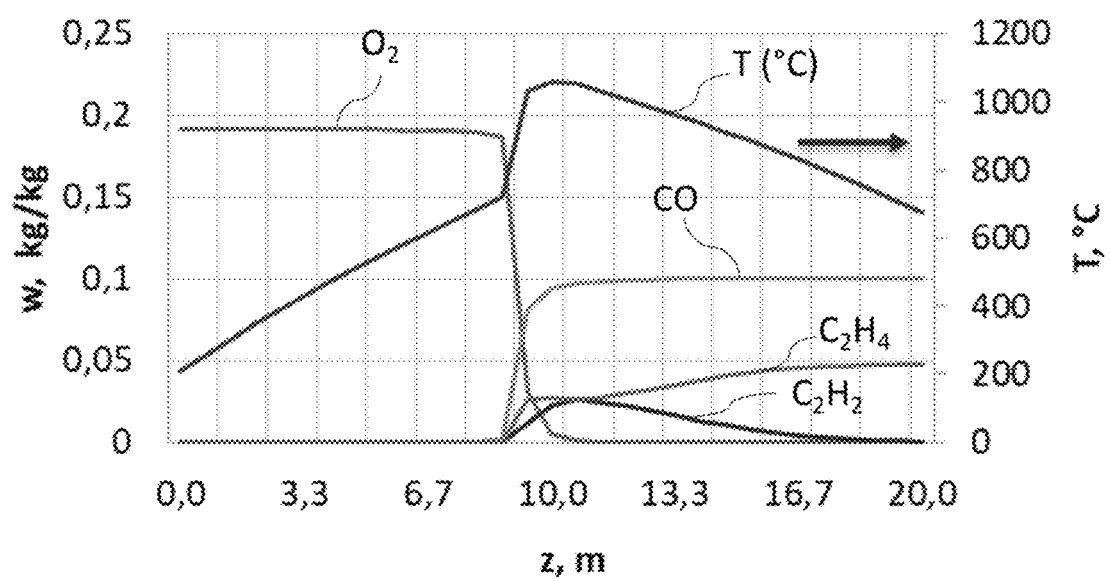
FIG. 5: high selectivity to $C_2H_4$ in the reactor with developed temperature and acetylene concentration profiles.

The concentration and temperature profiles along the reactor length are symmetrical in the tube and the shell for the first arrangement. FIGS. 3 and 4 show the temperature profiles along the length of the reactor for different cases (see Table 2). FIG. 3 shows a typical symmetrical profile that evolves in shell and tube. z=0 corresponds to the tube inlet/shell outlet.

Methane conversion and selectivity to different carbon-containing products are summarized in Tables 2 and 3.

TABLE 2

Conversion of $CH_4$, selectivity to carbon-containing products, $H_2$ to CO molar ratio, and production flowrate of $C_2H_4$ and CO at the outlet of reactor-heat exchanger for different inlet temperatures and [$CH_4/O_2$]$_0$. (Reaction conditions (tube or shell): P = 0.4 MPa, L = 20 m, Dt = 80 mm, Ds = 116 mm)

| [$CH_4/O_2$]$_0$, mol mol$^{-1}$ | 10.1 | 9.2 | 8.4 | 7.3 | 7.1 |
|---|---|---|---|---|---|
| $T_0$, °C. | 504 | 406 | 209 | 111 | 42 |
| V/F$_{CH4,0}$, m$^3$s mol$^{-1}$ | 0.09 | 0.09 | 0.09 | 0.09 | 0.09 |
| X(CH$_4$), % | 14.7 | 15.7 | 16.7 | 17.6 | 17.9 |
| S(C$_2$H$_4$), % | 40.0 | 39.9 | 40.4 | 36.8 | 36.4 |
| S(CO), % | 41.2 | 42.7 | 42.7 | 44.9 | 45.2 |
| S(C$_2$H$_6$), % | 3.4 | 4.3 | 5.2 | 4.7 | 47 |
| S(C$_2$H$_2$), % | 4.3 | 2.2 | 0.6 | 0.4 | 03 |
| S(CO$_2$), % | 5.0 | 5.9 | 6.7 | 9.3 | 9.7 |
| S(C$_3$H$_6$), % | 5.9 | 4.9 | 4.3 | 3.7 | 3.6 |
| [H$_2$/CO]$_{outlet}$, mol mol$^{-1}$ | 1.53 | 1.48 | 1.43 | 1.35 | 1.32 |
| m(C$_2$H$_4$), kg/day/reactor | 158 | 168 | 182 | 174 | 176 |
| m(CO), kg/day/reactor | 32 | 360 | 383 | 425 | 436 |

Comment: The remaining carbon-containing product that is not listed in the table is C$_3$H$_8$

TABLE 3

Conversion of CH$_4$, selectivity to carbon-containing products, H$_2$ to CO molar ratio, and production flowrate of C$_2$H$_4$ and CO at the outlet of reactor-heat exchanger for different inlet temperatures and [CH$_4$/O$_2$]$_0$ (Reaction conditions (tube or shell): P = 0.8 MPa, L = 20 m, Dt = 80 mm, Ds = 116 mm)

| [CH$_4$/O$_2$]$_0$, mol mol$^{-1}$ | 13.4 | 11.3 | 9.0 | 7.6 |
|---|---|---|---|---|
| $T_0$, °C. | 504 | 357 | 209 | 42 |
| V/F$_{CH4,0}$, m$^3$s mol$^{-1}$ | 0.0225 | 0.0225 | 0.0225 | 0.0225 |
| X(CH$_4$), % | 11.9 | 13.0 | 14. | 16.4 |
| S(C$_2$H$_4$), % | 45.6 | 41.3 | 40.1 | 37.7 |
| S(CO), % | 30.9 | 33.5 | 36.9 | 39.0 |
| S(C$_2$H$_6$), % | 6.8 | 10.7 | 7.8 | 7.6 |
| S(C$_2$H$_2$), % | 1.8 | 0.4 | 0.3 | 0.2 |
| S(CO$_2$), % | 3.3 | 4.8 | 6.7 | 8.4 |
| S(C$_3$H$_6$), % | 11.3 | 8.9 | 7.7 | 6.7 |
| [H$_2$/CO]$_{outlet}$, mol mol$^{-1}$ | 1.44 | 1.19 | 1.11 | 1.01 |
| m(C$_2$H$_4$), kg/day/reactor | 585 | 576 | 642 | 666 |
| m(CO), kg/day/reactor | 793 | 935 | 1182 | 1373 |

Comment: The remaining carbon-containing product that is not listed in the table is C$_3$H$_8$ Note that the inlet feed rate was 4 times higher at P=0.8 MPa, compared to that at P=0.4 MPa (see Table 3). Since the reaction rates are faster with an increase in pressure, the throughput can be increased for the same reactor geometry. At P=0.4 MPa, Re number in tube was in the range of 10 000-20 000, whereas in the shell it was 5 000-8 000 (Re number for the shell based on the hydraulic diameter DH=Ds, outer-Ds, inner). At P=0.8 MPa, Re number in tube was in the range 40 000-110 000, whereas in the shell it was 16 000-45 000. Therefore, apart from the higher throughput, fully turbulent regime, and therefore better heat transfer between the shell and tube is established at higher pressure, P=0.8 MPa.

It can be seen in Tables 2 and 3 that the selectivity to the desired products is high, higher than that observed at the outlet of an adiabatic reactor, or the one with isothermal operation (see comparative example). This can be explained by an interesting feature of the reactor—heat exchanger: namely, if it is focused on the tube side (the same phenomenon happens also on the shell side), the temperature along the reactor steadily rises due to the heat transfer from the shell to the tube side. At some point in the reactor, which preferentially lies in the middle of the reactor, sufficiently high temperature is reached to initiate the OCM reaction, oxygen is consumed and the temperature in the reactor reaches a peak, around 1050° C. This temperature results in increased acetylene production. However, continuing down the length of the reactor, now the heat is transferred from the tube to the shell side, the temperature starts decreasing, favouring the production of ethylene from the previously formed acetylene. This is also shown in FIG. 4.

Lower inlet temperature (at the end of the startup procedure), $T_0$, results in higher methane conversion, up to 17.9% (see Table 2), due to the higher amount of oxygen in the feed. Lower $T_0$ also results in lower acetylene production, due to the higher degree of cooling of the reaction products, as explained in the previous paragraph. However, the molar selectivity to undesired CO$_2$ slightly increases with a maximum of 9.7% at $T_0$=42° C.

Reactor operation at higher pressure, apart from the benefits described above, results in a slightly higher selectivity to C$_3$H$_6$ and slightly lower selectivity to CO$_2$.

Example 3—the Second Arrangement

The start-up step was conducted under the following conditions
For cases with a pressure of P=0.4 MPa
[CH$_4$/O$_2$]$_0$=30.0 mol mol-$^1$
F$_0$(CH$_4$)=4.0 kmol h$^{-1}$
$T_0$=750° C.
For cases with a pressure of P=0.8 MPa
[CH$_4$/O$_2$]$_0$=30.0 mol mol$^{-1}$ $F_0(CH_4)=16.0$ kmol h$^{-1}$ $T_0=750°$ C.

The second arrangement of the reactor produces similar results as described for the first arrangement. However, since the reaction mixture continues flowing from the tube to the shell side, the reactor is two times shorter, L=10 m, than the one reported for the first arrangement, and the production rates are, therefore, also two times lower (two last rows in Tables 4 and 5).

TABLE 4

Conversion of $CH_4$, selectivity to carbon-containing products, $H_2$ to CO molar ratio, and production flowrate of $C_2H_4$ and CO at the outlet of reactor-heat exchanger for different inlet temperatures and $[CH_4/O_2]_0$ (Reaction conditions (tube or shell): P = 0.4 MPa, L = 10 m, Dt = 80 mm, Ds = 116 mm)

| $[CH_4/O_2]_0$, mol mol$^{-1}$ | 10.3 | 9.4 | 9.0 | 7.6 | 7.3 |
|---|---|---|---|---|---|
| $T_0$, °C. | 504 | 406 | 307 | 209 | 42 |
| $V/F_{CH4,0}$, m$^3$s mol$^{-1}$ | 0.09 | 0.09 | 0.09 | 0.09 | 0.09 |
| $X(CH_4)$, % | 14.7 | 15.6 | 16.0 | 17.4 | 18.5 |
| $S(C_2H_4)$, % | 41.4 | 40.9 | 40.9 | 36.8 | 36.8 |
| S(CO), % | 40.2 | 41.8 | 42.1 | 45.4 | 44.4 |
| $S(C_2H_6)$, % | 3.6 | 4.3 | 4.9 | 4.7 | 5.4 |
| $S(C_2H_2)$, % | 4.1 | 2.2 | 1.1 | 0.8 | 0.3 |
| $S(CO_2)$, % | 4.3 | 5.3 | 6.1 | 8.3 | 7.5 |
| $S(C_3H_6)$, % | 6.2 | 5.2 | 4.7 | 3.7 | 3.6 |
| $[H_2/CO]_{outlet}$, mol mol$^{-1}$ | 1.55 | 1.48 | 1.45 | 1.40 | 1.37 |
| $m(C_2H_4)$, kg/day/reactor | 82 | 86 | 88 | 87 | 96 |
| m(CO), kg/day/reactor | 159 | 175 | 180 | 213 | 220 |

Comment: The remaining carbon-containing product that is not listed in the table is $C_3H_8$

TABLE 5

Conversion of $CH_4$, selectivity to carbon-containing products, $H_2$ to CO molar ratio, and production flowrate of $C_2H_4$ and CO at the outlet of reactor-heat exchanger for different inlet temperatures and $[CH_4/O_2]_0$ (Reaction conditions (tube or shell): P = 0.8 MPa, L = 10 m, Dt = 80 mm, Ds = 116 mm)

| $[CH_4/O_2]_0$, mol mol$^{-1}$ | 13.9 | 11.4 | 9.0 | 7.3 |
|---|---|---|---|---|
| $T_0$, °C. | 504 | 357 | 209 | 42 |
| $V/F_{CH4,0}$, m$^3$s mol$^{-1}$ | 0.0225 | 0.0225 | 0.0225 | 0.0225 |
| $X(CH_4)$, % | 11.9 | 12.9 | 15.3 | 17.5 |
| $S(C_2H_4)$, % | 46.5 | 42.0 | 40.8 | 35.3 |
| S(CO), % | 29.7 | 33.4 | 36.8 | 42.3 |
| $S(C_2H_6)$, % | 7.6 | 9.9 | 7.8 | 7.2 |
| $S(C_2H_2)$, % | 1.6 | 0.5 | 0.4 | 1.0 |
| $S(CO_2)$, % | 2.6 | 4.4 | 6.5 | 8.6 |
| $S(C_3H_6)$, % | 11.6 | 9.3 | 7.1 | 5.2 |
| $[H_2/CO]_{outlet}$, mol mol$^{-1}$ | 1.45 | 1.20 | 1.22 | 1.22 |
| $m(C_2H_4)$, kg/day/reactor | 298 | 292 | 337 | 333 |
| m(CO), kg/day/reactor | 379 | 463 | 607 | 795 |

Comment: The remaining carbon-containing product that is not listed in the table is $C_3H_8$ In this case, the reaction happens close to the point where the fluid continues flowing from the tube into the shell side. It is believed that this location of the reaction zone is preferable since a certain length of the reactor is needed to exchange the heat between the product mixture and reactor feed, and boost the selectivity to ethylene.

The second arrangement shows similar performance in terms of selectivity to products compared to the first arrangement.

For both arrangements, the reactor does not have to be in the form of straight tubes but can be also bent to occupy less space.

Example 4—Shorter Reactors

The start-up step was conducted under the following conditions

For cases with a reactor length of 5 m
$[CH_4/O_2]_0=30.0$ mol mol$^{-1}$
$F_0(CH_4)=12.0$ kmol h$^{-1}$
$T_0=750°$ C.

For cases with a reactor length of 2.5 m
$[CH_4/O_2]_0=30.0$ mol mol$^{-1}$
$F_0(CH_4)=12.0$ kmol h$^{-1}$
$T_0=750°$ C.

TABLE 6

Conversion of $CH_4$, selectivity to carbon-containing products, $H_2$ to CO molar ratio, and production flowrate of $C_2H_4$ and CO at the outlet of reactor-heat exchanger for different inlet temperatures and $[CH_4/O_2]_0$ (Reaction conditions (tube or shell): P = 1.5 MPa, L = 2.5 or 5 m, Dt = 80 mm, Ds = 116 mm)

| | 1$^{st}$ arrangement | 1$^{st}$ arrangement | 2$^{nd}$ arrangement | 2$^{nd}$ arrangement |
|---|---|---|---|---|
| L, m | 5 | 5 | 2.5 | 2.5 |
| $[CH_4/O_2]_0$, mol mol$^{-1}$ | 10.1 | 9.0 | 10.1 | 9.0 |
| P, MPa | 1.5 | 1.5 | 1.5 | 1.5 |
| $T_0$, °C. | 504 | 406 | 504 | 406 |
| $V/F_{CH4,0}$, m$^3$s mol$^{-1}$ | 0.00754 | 0.00754 | 0.00754 | 0.00754 |
| $X(CH_4)$, % | 13.6 | 14.6 | 13.7 | 14.8 |
| $S(C_2H_4)$, % | 38.3 | 37.1 | 37.1 | 36.2 |
| S(CO), % | 33.9 | 35.3 | 34.7 | 36.2 |
| $S(C_2H_6)$, % | 6.6 | 7.8 | 4.5 | 4.7 |
| $S(C_2H_2)$, % | 2.5 | 1.7 | 4.6 | 4.2 |
| $S(CO_2)$, % | 5.7 | 6.6 | 5.5 | 6.5 |
| $S(C_3H_6)$, % | 12.6 | 11.2 | 13.3 | 12.1 |
| $[H_2/CO]_{outlet}$, mol mol$^{-1}$ | 1.12 | 0.99 | 1.20 | 1.13 |
| $m(C_2H_4)$, kg/day/reactor | 422 | 438 | 206 | 216 |
| m(CO), kg/day/reactor | 746 | 831 | 384 | 432 |

Comment: The remaining carbon-containing product that is not listed in the table is $C_3H_8$ From the results it can be seen that the use of shorter reactors implies the use of higher temperature at the inlet.

The invention claimed is:

1. Process for a non-catalytic oxidative coupling of methane reaction characterized in that the process comprises:
    a step of providing a counter-current shell-tube reactor (1) comprising at least two tubes (3, 5) defining a tubular part (3) and a shell part (5) surrounding the tubular part (3) and at least one inlet (7, 9) to feed a gaseous feed stream (11) and at least one outlet (13, 15) to discharge a product stream (17);
    a step of providing a gaseous feed stream (11) comprising a gas mixture of methane ($CH_4$) and oxygen ($O_2$) in a defined molar ratio and preheated to a defined operating inlet temperature;
    a step of feeding the gaseous feed stream (11) at least in the tubular part (3) or at least in the shell part (15) of the counter-current shell-tube reactor (1);
    a step of non-catalytic oxidative coupling of the methane to form a product stream; and
    a step of recovering the product stream (17).

2. The process according to claim 1 characterized in that the counter-current shell-tube reactor (1) comprises two inlets (7, 9) and two outlets (13, 15) and in that the process comprises dividing the gaseous feed stream (11) into two portions (11a, 11b) defining a first gaseous feed stream portion (11a) and a second gaseous feed stream portion (11b) and a step of feeding the first gaseous feed stream portion (11a) in the tubular part (3) of the counter-current shell-tube reactor (1) using one inlet (7) and the second gaseous feed stream portion (11b) in the shell part (5) of the counter-current shell-tube reactor (1) using the other inlet (9) wherein the second gaseous feed stream portion (11b) flows counter-currently relative to the flow direction of the first gaseous feed stream portion (11a).

3. The process according to claim 1, characterized in that the counter-current shell-tube reactor (1) comprises one inlet (7) and one outlet (15) and in that the process comprises a step of feeding the gaseous feed stream (11) in the tubular part (3) of the counter-current shell-tube reactor (1) using the inlet (7); wherein a reaction mixture (19) exits the tubular part (3) and continues flowing into the shell part (5) in a counter-currently relative flow direction of the gaseous feed stream (11) in the tubular part (3).

4. The process according to claim 1, characterized in that the counter-current shell-tube reactor (1) comprises one inlet (9) and one outlet (13) and in that the process comprises a step of feeding the gaseous feed stream (11) in the shell part (5) of the counter-current shell-tube reactor (1) using the inlet (9); wherein a reaction mixture (19) exits the shell part (5) and continues flowing into the tubular part (3) in a counter-currently relative flow direction of the gaseous feed stream (11) in the shell part (5).

5. The process according to claim 1, characterized in that the tubular part comprises a single tube or a set of 2 or more tubes.

6. The process according to claim 1, characterized in that the process further comprises a start-up step of initiating the non-catalytic oxidative coupling of methane reaction; wherein the start-up step comprises providing a gaseous feed stream comprising a gas mixture of methane ($CH_4$) and oxygen ($O_2$) in an initial molar ratio of at least 25.0 wherein the gaseous feed stream is preheated to an initial inlet temperature of at least 750° C.

7. The process according to claim 6, characterized in that in the start-up step the gaseous feed stream has an initial molar ratio $CH_4:O_2$ ranging from 30.0 to 60.0 and/or in that the gaseous feed stream is preheated to an initial inlet temperature ranging from 750 to 1100° C.

8. The process according to claim 1, characterized in that the process comprises preheating the gaseous feed stream to an operating inlet temperature of at least 10° C.

9. The process according to claim 1, characterized in that the gaseous feed stream has an operating molar ratio $CH_4:O_2$ of at least 7.0.

10. The process according to claim 1, characterized in that the ratio of the volume of the reactor divided by the flow rate of methane in the feed stream (V/FCH4,0) is at most 0.1 $m^3s\ mol^{-1}$; and/or in that the process comprises an operating pressure in the reactor is ranging from 0.2 to 5.0 MPa.

11. The process according to claim 1, characterized in that the product stream comprises ethylene ($C_2H_4$) and ethane ($C_2H_6$), wherein the molar ratio $C_2H_4:C_2H_6$ is above 3.0.

12. The process according to claim 1, characterized in that the gaseous feed stream shows an operating molar ratio $CH_4:O_2$ ranging from 8.0 to 14.0 and an operating inlet temperature ranging from 200 to 550° C.

13. The process according to claim 1, characterized in that the gaseous feed stream shows an operating inlet temperature ranging from 30° C. to 300° C. and an operating pressure in the reactor ranging from 0.5 to 1.8 MPa.

14. The process according to claim 1, characterized in that the gaseous feed stream shows an operating inlet temperature ranging from 30° C. to 200° C., an operating pressure in the reactor ranging from 0.3 to 0.8 MPa; and gaseous feed stream shows an operating molar ratio $CH_4:O_2$ ranging from 7.0 to 9.0.

15. Method comprising providing the product stream (17) recovered in the process according to claim 1, and performing a reaction selected from a hydroformylation and a synthesis gas fermentation.

* * * * *